United States Patent [19]

Cox et al.

[11] 4,393,089

[45] Jul. 12, 1983

[54] MICROBIAL HETEROPOLYSACCHARIDE

[75] Inventors: Roger B. Cox, Reading; David C. Steer, Wirral, both of England

[73] Assignee: Lever Brothers Company, New York, N.Y.

[21] Appl. No.: 331,510

[22] Filed: Dec. 16, 1981

Related U.S. Application Data

[62] Division of Ser. No. 166,220, Jul. 7, 1980, Pat. No. 4,329,448.

[30] Foreign Application Priority Data

Jul. 10, 1979 [GB] United Kingdom ................ 7924040
Dec. 20, 1979 [GB] United Kingdom ................ 7943878

[51] Int. Cl.$^3$ ........................... A23L 1/04; A23L 1/24
[52] U.S. Cl. .................................... 426/573; 426/577; 426/578; 426/579; 426/565; 426/589; 426/605; 426/613; 426/658; 426/583; 426/590; 426/555; 426/622
[58] Field of Search ............... 426/573, 578, 579, 589, 426/605, 613, 658

[56] References Cited

U.S. PATENT DOCUMENTS

| 3,729,460 | 4/1973 | Patton | 426/579 |
|---|---|---|---|
| 3,960,832 | 6/1976 | Kang et al. | 426/579 |
| 4,006,262 | 2/1977 | Smith et al. | 426/579 |
| 4,012,333 | 3/1977 | Towle | 426/573 |
| 4,143,171 | 3/1979 | Buckley et al. | 426/573 |
| 4,298,725 | 11/1981 | Williams et al. | 426/658 |
| 4,326,052 | 4/1982 | Kang | 426/573 |
| 4,326,053 | 4/1982 | Kang | 426/573 |

Primary Examiner—Jeanette M. Hunter
Attorney, Agent, or Firm—James J. Farrell

[57] ABSTRACT

A food composition thickened or suspended with an heteropolysaccharide known as Biopolymer PS 87 comprises glucose, galactose, mannose, glucuronic acid and fucose. Bipolymer PS 87 is pseudoplastic, has a consistency at 20° C. of at least 150 poise and a yield stress value at 20° C. of at least 30 dynes/cm$^2$. Biopolymer PS 87 is synthesized by a strain of *Bacillus polymyxa* or a genetically similar micro-organism.

6 Claims, No Drawings

MICROBIAL HETEROPOLYSACCHARIDE

This is a divisional application of Ser. No. 166,220 filed July 7, 1980 now issued as U.S. Pat. No. 4,329,448.

The invention relates to a novel heteropolysaccharide and to a process for producing it by bacterial fermentation of an aqueous nutrient medium, and to an organism which produces the heteropolysaccharide. The invention also relates to compositions containing the heteropolysaccharide.

Certain polysaccharides can be obtained by microbial biosynthesis utilising specific strains or species of bacteria. It has been proposed, for example in Japanese patent specification No. 42-7600 (Meiji Seito KK), to culture a strain of *Bacillus polymyxa* known as "271" in a medium containing glucose or lactose to yield a polysaccharide composed of glucose, mannose, galactose and glucuronic acid in the approximate ratio of 8:7:3:5. The viscosity of a 1% solution of this polysaccharide at 25° C. is recorded as 6000 cP. The polysaccharide is stated to have a specific rotatory power of $[\alpha]_D^{28} = +92°$ and a molecular weight of about 10,000.

Also, the Kelco Corporation in their trade brochure dated March 1976 describing their product known as xanthan gum state that the gum, produced by fermentation with the organism *Xanthomonas campestris*, contains three different monosaccharides, namely mannose, glucose and glucuronic acid. Aqueous solutions of xanthan gum are described as pseudoplastic. The viscosity of a 1% solution of xanthan gum at a shear rate of 1 sec.$^{-1}$ appears to be of the order of 7000 cP. Xanthan gum is also believed to have a molecular weight of the order of at least 2,000,000.

Some of these polysaccharides have been employed as thickeners or suspending agents, particularly in waterbased systems such as foods, cosmetics and pharmaceuticals. Generally, however, it has been found that microbial polysaccharides have certain limitations when employed in such products, in terms of their ability to function as thickeners or suspending agents. Some polysaccharides are, for example, unstable, particularly when the products containing them are subjected to shear, for example when filling or dispensing through a narrow orifice. Limitations such as these can be partly overcome by increasing the concentration of the microbial polysaccharide in the product, but this can change the character of the product in other respects and can substantially increase raw material costs. Research has accordingly continued with the objective of discovering new polysaccharides that would be of value as improved thickeners or suspending agents, and which do not suffer from the aforementioned problems.

It has now been discovered that a novel heteropolysaccharide, referred to herein as Biopolymer PS 87, can be obtained by fermentation of a nutrient medium with a strain of the species of the bacterium known as *Bacillus polymyxa*. This heteropolysaccharide, which is useful, for example, as a thickener or suspending agent in foods, cosmetics and pharmaceuticals, has unexpectedly superior pseudo-plastic properties.

The invention accordingly provides a polysaccharide, known as Biopolymer PS 87, which comprises glucose, galactose, mannose and glucuronic acid, a 1% by weight solution of Biopolymer PS 87 having pseudo-plastic properties, a consistency at 20° C. of at least 150 poise and a yield stress value at 20° C. of at least 30 dynes/cm$^2$.

The Heteropolysaccharide

Biopolymer PS 87 has been shown by chemical analysis to comprise at least the following linked monosaccharide residues: glucose, galactose, mannose and glucuronic acid. Analysis for these monosaccharide residues was carried out following hydrolysis of a 1% solution of the heteropolysaccharide in 2 M trichloroacetic acid at 121° C. in a sealed tube for 1 hour. The hydrolysate so obtained containing monosaccharides was reduced in ammonium hydroxide with sodium borohydride for 1 hour at 20° C. The resulting alditols were acetylated with acetic anhydride in pyridine. The acetylated products were chromatographed and compared with standards using a Cyano-silicone OV225 column run isothermally at 190° C.

Glucuronic acid was identified in the heteropolysaccharide hydrolysate following formation of the lactone with hydrochloric acid and preparation and identification of gluconolactone trimethylsilyl ether derivative.

The glucuronic acid was quantified using a modified carbazole method.

Biopolymer PS 87 can also contain a minor amount of fucose.

From the results of this analysis, it was possible to calculate the percentage by weight of each of the constituent monosaccharide residues identified in Biopolymer PS 87.

The results obtained from several assays showed that each monosaccharide was present in Biopolymer PS 87 at percentages by weight within the following values:

|  | % w/w |
| --- | --- |
| glucose | from 40 to 45 |
| galactose | from 10 to 20 |
| mannose | from 25 to 30 |
| glucuronic acid | from 6 to 13 |
| fucose | from 0 to 1.5 |

The limits of each percentage range define the variation in results which can be obtained from the analysis of different samples of Biopolymer PS 87 obtained by bacterial fermentation, depending on culture medium used and culture conditions, such as temperature, pH and oxygen tension employed during fermentation.

As an example, the percentage by weight of the constituent monosaccharides of Biopolymer PS 87 from one particular fermentation run to be described later in this specification are:

|  | % w/w |
| --- | --- |
| glucose | 41 |
| galactose | 12 |
| mannose | 28 |
| glucuronic acid | 9 |
| fucose | 0.8 |

This sample of Biopolymer PS 87 accordingly comprised the monosaccharides in the following ratios:

|  | Molar ratio |
| --- | --- |
| glucose | 52 |
| galactose | 15 |
| mannose | 35 |
| glucuronic acid | 11 |

-continued

|  | Molar ratio |
| --- | --- |
| fucose | 1 |

It is to be understood that although the method of analysis of heteropolysaccharide described herein was the actual method used in arriving at the monosaccharide analysis set out above, other methods of monosaccharide analysis are available and can be used in determining the composition of Biopolymer PS 87.

Biopolymer PS 87 has a specific rotatory power of $[\alpha]_D^{25} = +60$ and a molecular weight of $34 \pm 4 \times 10^4$ as measured by low angle laser light scattering using Chromatix KMX-6 equipment. The molecular weight measurement was carried out at 25° C. over a concentration range of 0.01% to 0.1% by weight, the Biopolymer PS 87 samples being equilibrated against 0.1 M KCl.

Aqueous solutions of Biopolymer PS 87 are characterised by having an unexpectedly high consistency and an unexpectedly high yield stress value.

The consistency of a solution is defined as the apparent viscosity of that solution at a shear rate of 1 sec$^{-1}$, viscosity being the ratio of shear stress to shear rate.

The viscosity of aqueous solutions of Biopolymer PS 87 was measured at 20° C. using a Weissenberg Rheogoniometer, Model No. R18, fitted with a 5 cm cone and plate. This instrument was supplied by Sangamo Weston Ltd., North Lersted, Bognor Regis, Sussex, U.K. Viscosities of 86 and 182 poise were measured for 0.5% and 1.0% solutions of Biopolymer PS 87 respectively at a shear rate of 1.117 sec$^{-1}$. Values of 176 and 440 poise (0.5% and 1% solutions respectively) were measured at a lower shear rate of 0.353 sec$^{-1}$. These data show these solutions to be shear-thinning, i.e. pseudo-plastic. By interpolation of these results values for the consistency of the 1.0% solution was about 205 poise, and that of the 0.5% solution about 93 poise.

It can accordingly be stated generally that a 1% aqueous solution of Biopolymer PS 87 at 20° C. will have a consistency of at least 150 poise, preferably at least 200 poise.

The yield stress value of a solution is that shear stress which must be applied to the solution before it will flow. Solutions (1% w/w) of Biopolymer PS 87 have a yield stress, the magnitude of which can theoretically be measured by gradually applying a stress to the solution, e.g. that produced by the torque in a twisted wire in a rotational viscometer, the stress applied at the instant at which flow occurs being recorded. However, in practice, an accurate measurement of yield stress can be obtained more readily by applying a stress greater than the yield stress value and then removing the stress and allowing the viscometer to return to an equilibrium position. The equilibrium position, if the solution has a yield stress, will not be the original position of the unstressed system because the residual torque in the twisted wire will be balanced by the yield stress of the solution. Thus, by measurement of the residual torque, a measurement of the yield stress of the solution can be obtained.

This stress-relaxation technique was used to measure the yield stress of a 1% solution of Biopolymer PS 87 with the Weissenberg Rheogoniometer as described above, fitted with a 5 cm cone and plate. At a temperature of 20° C. and after 7½ hours (when equilibrium had been reached) a value of 54 dynes/cm$^2$ was recorded.

It can accordingly be stated generally that a 1% aqueous solution of Biopolymer PS 87 at 20° C. will have a yield stress value of at least 30 dynes/cm$^2$, preferably at least 50 dynes/cm$^2$. No other pseudo-plastic polysaccharide is known to exhibit a yield stress value as high as 30 dynes/cm$^2$ under these conditions of concentration and temperature. Indeed many polysaccharides do not possess the property of yield stress.

The high consistency and yield stress values of Biopolymer PS 87 can also be demonstrated by examining the ability of this heteropolysaccharide to suspend a particulate solid such as sand. To demonstrate this ability, a 0.5% w/v solution of the heteropolysaccharide was prepared in distilled water. 5 g acid washed silica sand of 44 to 60 mesh was then suspended in 100 ml of the heteropolysaccharide solution in a vessel having a 45 mm internal diameter. The suspension was held at a temperature of 25° C. $\pm 2°$ C. and the degree to which the sand sedimented was observed.

It was found that after 7 days, 76% by weight of the sand remained suspended in the upper 80% by volume of the solution. All other polysaccharides tested in a similar manner were unable to suspend sand for more than 2 days.

Micro-organisms

The invention also relates to a Biopolymer PS 87 producing strain of a micro-organism.

The micro-organism which is preferably employed in the production of Biopolymer PS 87 is a specific strain or mutant of the species *Bacillus polymyxa*.

The organism was isolated from seawater by plating out onto simple molasses plus mineral salts agar medium and incubating at 30° C. Those colonies which developed a mucoid or sticky appearance were streaked onto new plates of the same medium in order to obtain pure isolates of the organism.

The pure cultures were cultivated in liquid molasses-containing medium in shaken flasks at 30° C. to confirm a satisfactory growth pattern with an accompanying increase in viscosity indicative of polysaccharide production.

The pure culture of *Bacillus polymyxa* produced colonies of varying opacity. Translucent and opaque colonies could be separated by sub-culturing, and this variation appeared to be related to the extent of spore formation; the more opaque a colony, the more spores it contained. Four individual colonies were picked and submitted separately to the biochemical tests, the results of which are recorded below, and all gave the same results.

Colonies on nutrient agar were small, flat and white; those on potato-yeast-glucose agar were larger, darker and gummy.

The organism was a medium sized, straight, round-ended, motile, Gram-positive rod which formed spores. The spores were sub-terminal, large, oval, thick-walled and caused bulging of the cell.

The results of growth tests and biochemical tests are summarised as follows:
 Gram stain: positive
 acid and gas production from: arabinose, xylose, dextrin, fructose, galactose, glucose, glycerol, lactose, mannitol
 starch medium: hydrolysed
 gelatin medium: complete liquefaction in 14 days at 25° C.

casein medium: hydrolysed
indole formation: negative
citric acid utilisation: negative
chlorohydrate (0.25%) medium: no growth
sodium chloride (5%) medium: no growth
Voges-Proskauer test (acetylmethylcarbinol production): positive
litmus milk (25° C.): 3 days—slightly acid; 7 days—reduced, slight clot; 14 days—starting to digest, gassy
methyl red test: positive
hydrogen sulphide production: negative
catalase formation: positive
oxidase production: negative
growth in nutrient broth: 15° to 37° C. positive; 10° C. negative after 14 days; 41.5° C. negative after 14 days
good growth at pH 5.3
urease on Christensen's slope at 25° C. for 7 days: negative nitrate reduction: positive (very little nitrate produced and no residual nitrate).

It was concluded that on the basis of the above results and after consulting Bergy's "Manual of Determinative Bacteriology" (8th Edition) that the organism was a strain of *Bacillus polymyxa*.

A deposit of the strain of this organism was made in the National Collection of Industrial Bacteria, Torry Research Station, PO Box 31, 135 Abbey Road, Aberdeen, Scotland, on Aug. 2, 1978. The accession number allocated was NCIB 11429.

In addition to employing this particular strain of *Bacillus polymyxa* for the production of Biopolymer PS 87 is it also possible to employ genetically modified bacteria which have been adapted to synthesis Biopolymer PS 87.

The invention accordingly also relates to a micro-organism capable of synthesising Biopolymer PS 87 as a result of genetic transformation or conjugation, or modification by pasmids or plasmid hybrids or phage or phage hybrids, or other vectors, each carrying DNA specifying the synthesis of Biopolymer PS 87.

The basic organisms from which the modified organisms can be derived include the bacteria *E.coli*, Pseudomonas sp., Klebsiella sp., and Bacillus sp.

The invention also provides a method of making the genetically modified micro-organisms by incorporating into basic micro-organisms genetic information carrying the genes of the Biopolymer PS 87 synthesis mechanism.

One such method comprises the steps of:
(a) producing from the basic micro-organism a mutant deficient in genetic material specifying Biopolymer PS 87 synthesis,
(b) preparing a plasmid hybrid consisting of plasmid DNA covalently joined to DNA specifying Biopolymer PS 87 biosynthesis,
(c) introducing the plasmid hybrid into the Biopolymer PS 87 synthesis deficient basic micro-organism,
(d) culturing the resultant micro-organism in conditions favouring growth by the Biopolymer PS 87 synthesis mechanism, and
(e) selecting one or more clones of micro-organisms growing by the Biopolymer PS 87 synthesis mechanism.

Another such method comprises the steps of:
(a) producing from the basic micro-organism a mutant deficient in genetic material specifying Biopolymer PS 87 synthesis,
(b) identifying a phage DNA or a temperate phage for the basic micro-organism,
(c) introducing into the phage or phage DNA a piece of DNA specifying Biopolymer PS 87 synthesis, thereby to produce a phage hybrid,
(d) lysogenising the Biopolymer PS 87 synthesis deficient basic micro-organism with the phage hybrid,
(e) culturing the resultant micro-organism in conditions favouring growth by the Biopolymer PS 87 synthesis mechanism, and
(f) selecting one or more clones of micro-organisms exhibiting the Biopolymer PS 87 synthesis mechanism.

Suitable general techniques for making these modifications are described in UK patent specification No. 1,521,032, the disclosure of which is incorporated herein by reference.

The plasmids can be derived from any source, provided they are capable of transfer into one of the basic organisms. Suitable sources include *E.coli*, Pseudomonas sp., Klebsiella sp and Bacillus sp, especially *Bacillus polymyxa*.

The plasmid hybrid can be made directly from many plasmid sources including any present in the basic organism.

For the phage process, if the phage is used directly it should be of the type, including mutants, which include the basic organism in their natural host range. If phage DNA is used, this can be extracted from a natural phage or a phage that does not normally include the basic organism in its natural host range.

Suitable methods for deriving the plasmids or obtaining the plasmid hybrids and also suitable methods for using a phage or a phage hybrid for extracting a phage DNA are described in UK patent specification No. 2,003,926, the disclosure of which is incorporated herein by reference.

The Process

The invention also provides a process for the production of Biopolymer PS 87 which comprises the steps of
(i) cultivating a strain of a micro-organism containing genetic material specifying Biopolymer PS 87 synthesis under submerged aerobic conditions in an aqueous culture medium comprising a source of carbon, a source of nitrogen, a source of iron, a source of magnesium and a source of phosphorus, the pH of the culture medium being maintained at a value of from 4.5 to 7.5, until substantial formation of Biopolymer PS 87 has occurred, and
(ii) isolating Biopolymer PS 87 from the culture medium.

The genetic material is, for example, chromosomal DNA or DNA of plasmid or plasmid hybrid or DNA of phage or phage hybrid.

According to a preferred embodiment of the invention, a process for the production of Biopolymer PS 87 is provided in which the micro-organism is a bacterium of the species Bacillus, preferably *Bacillus polymyxa*. One such process comprises the steps of:
(i) cultivating *Bacillus polymyxa* NCIB 11429 under submerged aerobic conditions in an aqueous nutrient medium having a pH of from 4.5 to 7.5, until substantial accumulation of Biopolymer PS 87 has occurred;

(ii) heating the culture medium to a temperature of at least 50° C. at a pH value of at least 8; and
(iii) subsequently separating coagulated cells and cell debris from the culture medium to provide a visually clear solution of Biopolymer PS 87.

The process can be carried out on a batch basis or as a continuous operation or by other suitable means.

According to a preferred method of carrying out the first step of the process of the invention, a suitable aqueous nutrient culture medium is inoculated with *Bacillus polymyxa* NCIB 11429 and incubated to cultivate this organism at a temperature of from 25° to 40° C., preferably from 30° to 35° C., for a period of about 45 to 60 hours.

The aqueous nutrient medium will normally contain a source of carbon, preferably comprising at least one monosaccharide or disaccharide at a concentration of about 1 to 5% by weight, preferably about 2 to 3% by weight. Suitable sources of carbon are, for example, glucose, sucrose, maltose, fructose, mannose, starch, starch hydrolysate or corn syrup. Preferably, the carbon source employed is glucose. Crude sources of monosaccharide or disaccharide such as molasses, whey or whey ultrafiltrate may also be used.

The medium will also normally contain a source of nitrogen which can be organic in nature as, for example, soya protein, an enzymatic digest of soya bean meal, distillers solubles, corn steep liquor, yeast extract, or casein hydrolysate. When utilising an organic nitrogen source in the aqueous culture medium, it can be present in an amount of from about 0.05 to 0.5% by weight of the medium, to provide approximately 0.01 to 0.1% by weight of nitrogen. Alternatively, it is possible to have present in the culture medium an inorganic nitrogen source such as ammonia, ammonium nitrate, ammonium chloride, ammonium sulphate or ammonium acetate. The amount of the inorganic nitrogen source which can be employed can form up to 0.5%. It is furthermore possible to employ a mixture of organic and inorganic nitrogen. The medium will also normally contain sources of other elements such as potassium, sodium, magnesium, phosphorus and trace metals, including manganese, iron, zinc, calcium, copper and cobalt, which are required for normal growth and polysaccharide production.

The medium will also preferably contain a trace amount of from about 0.5 to about 5/mg/l of biotin. This can be provided as biotin itself or a source of biotin such as yeast extract or molasses.

The pH of the aqueous culture medium is important for adequate growth of the bacterium and formation of Biopolymer PS 87. The optimum pH value for production of the Biopolymer PS 87 is from 4.5 to 7.5. Control of the pH can generally be achieved by use of a buffer such as dipotassium acid phosphate at a concentration of from about 0.1 to 1% by weight of the medium. Any of the following examples of sodium or potassium salts of phosphoric acid may be used as a buffer: $KH_2PO_4$, $K_2HPO_4$, $K_3PO_4$, $NaH_2PO_4$, $Na_2HPO_4$, or $Na_3PO_4$.

The pH can if necessary be controlled by using a pH meter coupled with a source of a suitable base such as an alkali metal hydroxide, for example potassium or sodium hydroxide. As the pH is lowered due to the production of acid as bacterial growth proceeds, small quantities of the potassium or sodium hydroxide solution can be automatically added to keep the pH within the desired range.

Generally, however, for batch fermentation, the process of the invention does not require the addition of alkali to control the pH of the culture medium. It has been observed that the pH usually drops to about 5 after 10 to 20 hours, and then increases to about 6 to 7 and generally remains at this level for the remainder of the incubation period. For continuous fermentation, it may be necessary to control the pH of the fermentation medium by one of the methods described herein.

In order to obtain rapid and efficient production of the heteropolysaccharide, it is essential to have a sufficient quantity of oxygen available for growth of *Bacillus polymyxa* NCIB 11429. If too little oxygen is available in the culture medium, production of the heteropolysaccharide by the bacterium is likely to be poor. The conditions of agitation and aeration should preferably be such that a rate of oxygen transfer from gaseous to liquid phase of at least 0.05 g/l/hour is provided.

In order effectively to separate, according to the second and third process step of the invention, the heteropolysaccharide so produced from bacterial cells and cell debris in the culture medium, it is necessary to contact the culture medium either before or after heating it to a temperature of at least 50° C., with an alkali to raise the pH of the culture medium to a value above pH 7. Bacterial cells and cell debris can thereby be flocculated in such a manner that they can readily be separated from the culture medium to leave a visually clear supernatant which contains the heteropolysaccharide in solution.

Separation of coagulated cells and cell debris from the culture medium can be further facilitated by heating the culture medium in the presence of a calcium salt, such as calcium chloride or calcium nitrate. For this purpose, the calcium salt can comprise up to 0.2%, preferably from 0.05% to 0.1%, by weight of the culture medium.

It is apparent that other more conventional methods of separating cells and cell debris from the culture supernatant, for example filtration or centrifugation without the pre-treatments as herein described, are not successful in that cell or cell debris removal is inefficient and aqueous solutions of the heteropolysaccharide are always turbid.

According to a preferred process for separating the heteropolysaccharide from the culture medium, the medium is first heated to a temperature of at least 50° C., preferably to a temperature of from 60° to 70° C., and then the pH of the medium is adjusted to a value above pH 7, usually at least pH 8, and preferably to a value of from pH 8 to pH 11. This is conveniently effected by the addition of an alkali such as sodium hydroxide, although other alkalis can be used.

For best results, the culture medium is again heated, this time to a temperature of at least 75° C., preferably from 80° to 95° C., in the presence of added calcium chloride at a concentration of 0.08% by weight of the culture medium, for sufficient time to complete flocculation of bacterial cells and cell debris. The flocculated cells and cell debris can then readily be separated by, for example, static gravity sedimentation, by centrifugation or by filtration, to leave a visually clear supernatant containing Biopolymer PS 87 in solution.

Biopolymer PS 87 may be recovered by treatment of the visually clear culture medium supernatant with a water-miscible organic liquid in which the heteropolysaccharide is substantially insoluble and which does not react with it. In this way, the heteropolysaccharide can be precipitated from solution. The quantity of organic liquid employed will generally be from 1 to 2 volumes per volume of culture supernatant. Examples of suitable organic liquids that may be employed are acetone and $C_1$ to $C_5$ alkanols such as methanol, ethanol, isopropanol, 2-butanol and tert-butanol. Isopropanol and methanol are the preferred organic liquids. The heteropolysaccharide is finally recovered by separating it from the organic liquid, for example by filtration, and then drying it.

EXAMPLES ILLUSTRATING THE PROCESS FOR THE PRODUCTION OF BIOPOLYMER PS 87

EXAMPLE 1

This example illustrates the production of Biopolymer PS 87 by batch fermentation of a sucrose/yeast extract medium with *Bacillus polymyxa* NCIB 11429. The medium contained the following ingredients:

|  | % w/v |
|---|---|
| Sucrose | 5.0 |
| Yeast extract | 0.5 |
| $K_2HPO_4$ | 0.25 |
| $MgSO_4.7H_2O$ | 0.1 |
| Trace element solution | 0.4 |
| Water | to 100 |

The trace element solution contained the following ingredients:

|  | % w/v |
|---|---|
| $MnSO_4.4H_2O$ | 0.3 |
| $FeSO_4.7H_2O$ | 0.9 |
| $ZnSO_4.7H_2O$ | 1.8 |
| $CuSO_4.5H_2O$ | 0.08 |
| $CoCl_2.6H_2O$ | 0.09 |
| Conc. $H_2SO_4$ | 0.5 |
| Water | to 100 |

20 l of this medium was sterilised in a 28 l New Brunswick Fermenter. The fermenter was fitted with automatic pH control (addition of 5% NaOH), a dissolved-oxygen probe, an antifoam probe and an impeller. Silicone (DC, MS, A) antifoam compound (Hopkins and Williams, from Dow Chemicals) was used to control foaming which occurred during the early part of the fermentation.

The fermenter was inoculated with 400 ml of a 48 hour shake flask culture, which was highly viscous, foaming, and had a pH of 5.3. Initially, the impeller speed was 100 rpm with a sparged air rate of 15 liters/min. Temperature was maintained at 30° C. Dissolved oxygen tension (DOT) rapidly fell to a minimum of less than 2% and remained low as the pH of the broth dropped to 4.8 from an initial value of 7.4. The pH gradually increased from this minimum over the next few hours, but there appeared to be little increase in viscosity of the broth. The pH of the fermentation broth was raised to pH 6 and maintained at that value, and the impeller speed was increased to 200 rpm. The broth became more viscous as the fermentation proceeded; final viscosity was 250 poise at a shear rate of 1 $sec^{-1}$ (25° C.). The heteropolysaccharide concentration was 9 g/l (equivalent to an 18% yield based on the sugar supplied).

The heteropolysaccharide-containing broth was diluted by the slow addition of isopropyl alcohol (IPA) to a concentration of 30% (v/v) and the bacterial cells were removed by centrifugation at 20,000 g for 1 hour at ambient temperature. The supernatant was mixed with more IPA to increase the concentration to 70%. This completed the precipitation of the heteropolysaccharide. The IPA water mixture was discarded and the heteropolysaccharide was dried in an oven. This preparation could be readily reconstituted in water to give homogenous viscous solutions.

EXAMPLE 2

In this example the fermentation medium was the same as described in Example 1 except that yeast extract was included at 0.4% (w/v) and the sucrose was replaced by glucose at 2.0% (w/v). The medium (22 liters) was inoculated with 1 liter of a 3 day old shake flask culute of *Bacillus polymyxa* NCIB 11429. The pH dropped gradually from an initial value of 6.9 to a value of 6.0 after 20 hours fermentation. The pH was prevented from falling below this value by the addition of 5% NaOH. The polysaccharide concentration in the fermentation broth was determined in samples taken at regular intervals, the maximum concentration (0.4%, which is equivalent to a 20% yield) was obtained about 45 hours after the start of the fermentation. At this point the fermentation was considered complete as judged by exhaustion of glucose feedstock and an increase in the dissolved oxygen concentration to a value approaching saturation. The final pH of the broth was 6.6.

EXAMPLE 3

This example illustrates the production of Biopolymer PS 87 in continuous fermentation. The medium used was similar to that described in Example 2 except that the concentration of $K_2HPO_4$ was reduced to 0.15% and, in addition, 0.1% $Na_2HPO_4$ was included. A 3 liter stirred tank fermenter was used and the fermentation volume was maintained at 1.5 liters. Foaming was prevented by the intermittant addition of antifoam reagent. An adjustable peristaltic pump controlled the rate of flow into the fermenter and a weir was used to control the level of the liquid.

The concentration of heteropolysaccharide was determined in samples of the broth taken at a series of dilution rates ranging from 0.03–0.10 (i.e. residence times of 33 hours and 10 hours respectively). The concentration of polysaccharide in the broth was found to increase with decreasing dilution rate (D), i.e. from about 0.4% at D=0.1 to about 0.8% (D=0.03).

EXAMPLE 4

Continuous fermentation to produce Biopolymer PS 87 was carried out in a manner similar to that described in Example 3 using media based on whey and whey permeate. The fermentation was operated for 10 days on medium A and for a further 20 days on medium B, after which time there was no deterioration in polysaccharide quality or quantity.

| Medium A | Medium B |
|---|---|
| Whey permeate diluted 1:1 with tap water | Whole whey diluted 1:1 with tap water |
| 0.2% yeast extract | 0.2% yeast extract |
| 0.4% trace element solution* | 0.4% trace element solution* |

*For details of trace elements see Example 1.

The fermentation volume was maintained at about 1.8 liters. A peristaltic pump drew media through the overflow into a chilled collection vessel. A 7 cm, 6 bladed impeller was used. Speeds of between 1200–1500 rpm were found to be necessary to keep the broth moving depending on its thickness.

The pH was controlled at 6.6 with a sodium hydroxide solution (5% w/v). Air was supplied at 500 ml/min. The dissolved oxygen was controlled between about 40%–50% by supplementing the air supply with 100 ml/min of oxygen when the dissolved oxygen fell below a pre-set level. No anti-foam additions were necessary. The medium was sterilised before introduction into the fermenter for 40 minutes at 115° C.

The effect of varying the dilution rate on the polysaccharide was examined. Because of the large and variable gas hold up in the fermenter it proved difficult to accurately estimate the liquid volume. This leads to similarly large error when estimating the dilution rate. The dilution rate was varied between 0.04–0.1 hr$^{-1}$±10%. Tabulated below are the polysaccharide concentrations produced at steady state for Medium B.

| Dilution rate hr (±10%) | Polysaccharide concentration % w/v | Yield (%) |
| --- | --- | --- |
| 0.04 | 0.93 | 46 |
| 0.04 | 0.91 | 45 |
| 0.07 | 0.71 | 35 |
| 0.08 | 0.59 | 30 |
| 0.10 | 0.53 | 26 |
| 0.10 | 0.47 | 23 |

EXAMPLE 5

The invention is also illustrated by the following example which describes the production of the heteropolysaccharide Biopolymer PS 87 by continuous fermentation of a glucose yeast extract medium with *Bacillus polymyxa* NCIB 11429.

The medium contained the following ingredients:

| | % w/v |
| --- | --- |
| Glucose | 2.0 |
| Yeast extract | 0.4 |
| K$_2$HPO$_4$ | 0.15 |
| Na$_2$HPO$_4$ | 0.1 |
| MgSO$_4$ 7H$_2$O | 0.1 |
| Trace element solution | 0.4 |
| Water | to 100 |

The trace element solution contained the following ingredients:

| | % w/v |
| --- | --- |
| MnSO$_4$ 4H$_2$O | 0.2 |
| FeCl$_3$ | 0.7 |
| ZnCl$_2$ | 0.1 |
| CuCl$_2$ 2H$_2$O | 0.03 |
| CoCl$_2$ 6H$_2$O | 0.05 |
| CaCl$_2$ 6H$_2$O | 0.5 |
| Conc HCl | 0.5 |
| Water | to 100 |

1.5 l of this medium were sterilised in a 3 l stirred tank fermenter by heating for 40 minutes at 115° C. The fermenter was fitted with automatic pH control (using 5% NaOH), a dissolved oxygen tension probe, an antifoam probe and an impeller. Silicone antifoam compound (ex Dow Chemicals) was used to control foaming as and when necessary.

Fermentation was initiated by inoculating the 1.5 l of the medium with 100 ml of a 48 hour shake flask culture of the organism. The medium was incubated for 2 days under the following conditions:

| Temperature | 32° C. |
| --- | --- |
| Air rate | 0.5 l/min |
| Dissolved oxygen tension | 40 to 50% |
| pH | 6.5 to 7.0 |

The medium was stirred continuously using a 7 cm, 6-bladed impeller at a speed, initially of 500 rpm, increasing to 1200 rpm at 2 days as viscosity of the medium increased.

After incubation for 2 days, the fermenter was connected to a bulk supply medium which had been sterilised at 121° C. for 10 minutes, and continuous feed of fresh medium to the fermenter was started. Fermented medium was withdrawn from the fermenter so as to maintain the volume of medium within the fermenter at approximately 1.5 l. An adjustable peristaltic pump controlled the rate of flow of medium into the fermenter and a weir was used to control the level of the medium.

The flow rate was adjusted to a value of from 45 to 150 ml/hr. The dilution rate of the medium expressed as $$D=(F/V)$$

where
D is the dilution rate,
F is the flow rate in l/hr, and
V is the fermentation volume in liters, was accordingly maintained within the range of 0.03 to 0.1.

The concentration of heteropolysaccharide was determined in samples of the fermented culture medium taken at a series of dilution rates within this range and it was found to increase with decreasing dilution rate (D), i.e. from about 0.4% at D=0.1 to about 0.8% (D=0.03).

The temperature, air flow rate, dissolved oxygen tension and pH were maintained at or about the values employed during the 2-day run up before continuous feed was started.

Continuous culture can be maintained indefinitely, but in one experiment a 50 day run was achieved without problems.

The heteropolysaccharide Biopolymer PS 87 was isolated from the fermented culture medium drawn from the fermenter in the following manner:

A 3 l portion of this medium was heated to a temperature of 60° C. with constant mixing using a paddle type stirrer. The pH was then adjusted to pH 9.0 by the addition of 5% NaOH solution, 2.4 g calcium chloride was added and the medium transferred to a conical flask which was placed in an oven at 85° C. for 12 hours. During this period flocculation of the bacterial cells and cell debris took place. The majority of the flocs sedimented to the bottom, but a proportion floated to the surface, presumably due to adhering gas bubbles. Between these two layers of cell material a zone of clear liquid was present; this was removed by suction and a total of 2 l of clear liquid was collected. After cooling, 3 l of isopropyl alcohol was added to this liquid with mixing. A stringy precipitate of polysaccharide was obtained which was recovered and vacuum dried. The yield was 11 g.

The heteropolysaccharide when redissolved in water at a concentration of 1% w/v yielded a solution having a consistency at 20° C. of about 200 poise and a yield stress at 20° C. of about 54 dynes.

Domestic and Industrial uses of Biopolymer PS 87

The invention also provides aqueous products or a dry mix suitable for preparing aqueous products on the addition of water, which products comprise Biopolymer PS 87.

The unique physical properties of Biopolymer PS 87 enables it to be employed in a wide range of domestic and industrial applications as suspending agents, emulsifiers, flocculation agents, stabilisers and thickeners.

The following are examples of products, processes and applications which can benefit from the use of Biopolymer PS 87.

Milk product

The invention also relates to edible products, particularly to a milk-gelling composition.

Milk puddings which contain a tetra-alkali metal pyrophosphate and an edible calcium salt are well known: see, for example, U.S. Pat. No. 2,607,692 which discloses such a pudding. As an additional ingredient, milk puddings usually require the presence of a dry pregelatinised starch. The milk gels produced from these compositions have a pasty or starchy consistency and are prone to exhibit objectionable liquid separation, i.e. syneresis, on aging.

The invention accordingly also provides a composition comprising a mixture of a tetra-alkali metal pyrophosphate, an edible calcium salt, and Biopolymer PS 87. These ingredients, preferably as a dry finely-divided composition, can be agitated with cold milk to form a milk gel.

The tetra-alkali metal pyrophosphate can be, for example, tetrasodium pyrophosphate, or tetrapotassium pyrophosphate. Examples of appropriate edible water-soluble calcium salts are calcium acetate, calcium lactate, calcium sulphate, calcium citrate, calcium gluconate, calcium propionate, calcium saccharate and calcium tartrate.

The quantities of tetra-alkali metal pyrophosphate, edible calcium salt and Biopolymer PS 87 may be varied depending upon the particular properties desired in the milk pudding product. In general, however, it can be stated that a suitable preparation for use in the invention comprises by weight from 1.5 to 3.5 parts of a tetra-alkali metal pyrophosphate, from 1 to 5 parts of an edible calcium salt, and from 0.5 to 4 parts of Biopolymer PS 87.

In forming a milk gel or milk pudding according to the invention, a homogeneous dry blend of the gelling composition, as defined above, is added to cold milk and the ingredients are blended in with a mixer. The mixed material is then poured into a suitable container after which the mixture is preferably refrigerated. After approximately 15 minutes, the mixture will have set sufficiently to eat.

In addition to the essential gelling components included in the composition, there can also be included other ingredients which are normally used for flavouring and colouring of milk puddings. For example, there can be included any of the usual flavourings such as cocoa, vanilla, cinnamon, or fruit or nuts such as pecans, raisins, bananas, figs, or dates. Moreover, there can be included also an anti-foaming agent such as an edible oil, e.g. safflower oil, coconut oil, peanut oil, or cottonseed oil.

In forming a milk pudding from the composition, either whole milk or liquid skim milk can be employed. Further, the milk can be replaced altogether by adding dry milk solids, derived either from whole or skim milk, to the dry solids, derived either from whole or skim milk, to the dry mix. In this case, the addition of water and agitation of the resulting mixture are all that is necessary for the preparation of a milk pudding.

In order to further illustrate the invention, there are presented the following examples.

EXAMPLE 6

A mixture can be formed by blending the following dry ingredients in the amounts indicated.

|  | Parts by weight |
| --- | --- |
| Sugar | 80.0 |
| Cocoa | 15.0 |
| Vanilla flavour | 0.3 |
| Salt | 1.0 |
| Biopolymer PS 87 | 1.0 |
| Tetrasodium pyrophosphate | 2.5 |
| Calcium gluconate | 4.0 |

The above ingredients in a comminuted form can be suitably mixed to give a homogeneous mixture and then added to 568 ml of cold milk and mixed for 3 minutes with an egg beater. The mixture should be poured into a container and refrigerated. After about 15 minutes, the mixture will have set to form a milk pudding having a very smooth texture, a short body which breaks down readily to give a very clean mouth-feel, and stability to syneresis.

EXAMPLE 7

A mixture of dry ingredients in finely comminuted form can be blended to form a homogeneous dry mix in the following proportions:

|  | Parts by weight |
| --- | --- |
| Sugar | 80.00 |
| Vanilla flavour | 0.40 |
| Tartrazine (the trisodium salt of 3-carboxy-5-hydroxy-1-p-sulphophenyl-4-p-sulphophenyl-azapyrazole) | 0.02 |
| Sunset yellow FCF (the disodium salt of 1-p-sulphophenylazo-2-naphthol-6-sulphonic acid) | 0.005 |
| Salt | 1.00 |
| Biopolymer PS 87 | 1.00 |
| Tetrasodium pyrophosphate | 2.50 |
| Calcium gluconate | 4.00 |

The above mixture should be blended with 568 ml of milk for several minutes using an egg beater, after which is can then be poured into a suitable container. The mixture should then be refrigerated for about 15 minutes. At this point, the mixture will have set sufficiently to eat. The resulting product will have a very smooth texture, a short body which breaks down readily to give a very clean mouth-feel, and stability toward syneresis.

Milk products of the type herein described are given in BP 1,257,057, the disclosure of which is incorporated herein by reference.

Salad dressing

The invention also relates to a salad dressing.

Salad dressings cannot usually be subjected to freezing and thawing without textural deterioration which can result in breakage of the emulsion so as to cause almost total oil separation from the dressing after thawing. The present invention is accordingly concerned with a salad dressing which has freeze-thaw stability, and with a method of preparing such a salad dressing.

A salad dressing is the emulsified semi-solid food prepared from edible vegetable oil, an acidifying ingredient, an egg-yolk-containing ingredient and a cooked or partly cooked starchy paste prepared with a food starch, tapioca flour, wheat flour, rye flour or any two or more of these.

In addition, a salad dressing may be seasoned or flavoured with various ingredients, such as salt, and/or monosodium glutamate, a sweetening ingredient, such as sugar, dextrose, corn syrup, invert sugar syrup, non-diastatic maltose syrup, glocuse syrup, and honey, other flavouring ingredients such as mustard, paprika, other spice, or any spice oil or spice extract.

Accordingly, the invention provides a salad dressing comprising an edible oil, water, an emulsifier, cooked starch, an acidifying agent, salt and Biopolymer PS 87.

Suitable edible oils include vegetable oils such as cottonseed oil, soyabean oil, safflower oil, corn oil and olive oil. The amount of oil in the salad dressing will usually form from 30 to 70%, preferably from 40 to 50% by weight of the dressing.

The acidifying ingredient present in the salad dressing prepared according to the invention may include vinegar, lime juice, or lemon juice. The quantity of acidifying ingredients which may be employed is equivalent to a content of glacial acetic acid in the final food product ranging from 1 to 1.5% by weight.

A further ingredient is an emulsifier, for example an egg-yolk-containing ingredient or a synthetic emulsifier such as that identified by the trade name "TWEEN 60" (polyoxyethylene sorbitan monostearate). The quantity of emulsifier which may be present in the salad dressing is from 0.25 to 4% by weight of the total weight of the food product. A still further ingredient which is present in the salad dressing is salt in an amount from 1% to 3.5% by weight of the fial product.

In addition to the foregoing ingredients, the salad dressing also contains Biopolymer PS 87 in an amount of from 0.2 to 0.3% by weight.

The invention also provides a method of making a spoonable salad dressing which dressing contains an edible oil in an amount of from 30% to 70% by weight of said dressing; water in an amount of from 30% to 70% by weight of salad dressing; emulsifier in an amount effective to form an emulsion; cooked starch in an amount sufficient to provide the characteristic body of a spoonable salad dressing; acidifying ingredient, such as glacial acetic acid equivalent, in an amount of from 1% to 1.5% by weight of said dressing; Biopolymer PS 87 in an amount of from 0.2% to 0.3% by weight of said dressing; and salt in an amount of from 1.0% to 3.5% by weight of said dressing, which method comprises forming a first mixture containing Biopolymer PS 87 and about one-half of the water; forming a second mixture comprising the balance of the water together with the cooked starch, the emulsifier, and an amount of the salt ranging up to about 0.75% by weight of the dressing; blending the first mixture and said second mixture to form a combined first-second mixture; stirring the combined first-second mixture with the edible oil and with the acidifying ingredient until a substantially uniform mixture is obtained; emulsifying the uniform mixture; and then dispersing the remainder of the salt into the emulsified mixture to obtain a spoonable salad dressing.

This aspect of the invention is illustrated by the following Example.

EXAMPLE 8

A typical salad dressing prepared according to the invention can contain the following ingredients in the stated weight percentages:

|  | % w/w |
|---|---|
| Biopolymer PS 87 | 0.3 |
| HPC starch (National Starch Co.) | 2.5 |
| Sugar | 10.0 |
| Salt | 2.0 |
| Mustard (powdered) | 0.5 |
| Egg-yolk (raw) | 4.0 |
| Vegetable oil | 30.0 |
| Vinegar (white) 100 gr. | 10.0 |
| Water | 40.7 |

In preparing the above salad dressing the Biopolymer PS 87, sugar and mustard can be added to half the total amount of the water with vigorous stirring. Stirring should be continued for 30 minutes to form a first mixture. Following this, 35% of the total amount of salt should be added to the remaining portion of water along with the starch. This mixture should then be heated for a sufficient time to cause complete hydration of the starch. Thereafter, the mixture should be allowed to cool and the egg yolk added and thoroughly mixed in to form a second mixture.

The first and second mixtures should then be thoroughly mixed and oil added, slowly at first, and then at a rapid rate with complete addition taking about two minutes with stirring. Following this, the vinegar should be added with stirring until the mixture is uniform. The mixture should then be passed through a colloid mill, adding the remainder of the salt and dispersing in the mixture.

Other salad dressings which can be prepared using the above-described procedure should contain the following ingredients:

|  | % w/w | |
|---|---|---|
| Biopolymer PS 87 | 0.3 | 0.3 |
| HPC starch (National Starch Co.) | 2.5 | 2.5 |
| Sugar | 10.0 | 10.0 |
| Salt | 2.0 | 2.0 |
| Mustard (powdered) | 0.5 | 0.5 |
| Egg-yolk (raw) | 4.0 | 4.0 |
| Vegetable oil | 35.0 | 40.0 |
| Vinegar (white) 100 gr. | 10.0 | 10.0 |
| Water | 35.7 | 30.7 |

The above salad dressings, containing the listed ingredients in the amounts shown in percent by weight are spoonable dressings having the desirable temperature stability.

The salad dressings so prepared are stable to freeze-thaw cycling.

This aspect of the invention is similar to that described in U.S. Pat. No. 3,676,157, the description of which is incorporated herein by reference.

Dehydrated food product

The invention also relates to dehydrated food products and to methods for improving the hydration of dehydrated foods by including therein Biopolymer PS 87.

The art of dehydrating foods is an ancient one, and men for centuries have desired to remove moisture from food material so as to reduce its weight and bulk, thus making it easier to store and transport, and more especially to decrease the likelihood of food spoilage, thus making it possible to successfully store food longer by discouraging the growth of micro-organisms which require a high level of moisture for growth.

Although dehydrated foods clearly have advantages, the reconstitution of dehydrated foods with water still presents problems, which include the excessive time required to reach full rehydration and the inability to obtain a quality as good as the fresh counterpart.

This invention is accordingly concerned with food products which are rehydrated or hydrated more rapidly and more completely, especially in the case of dried or dehydrated foods, and provides a method for achieving this aim.

Accordingly, the invention provides a dehydrated food product comprising dry Biopolymer PS 87 and a dry food ingredient, Biopolymer PS 87 being present in the food product in an amount of from 0.01 to 1.5% by weight of the hydrated weight of the food product.

A preferred amount of Biopolymer PS 87 is from 0.1 to 0.9% by weight of the hydrated weight of the food product.

The invention also provides a process for preparing a dehydrated food product, which comprises mixing dry Biopolymer PS 87 with a dry food ingredient, the Biopolymer PS 87 being present in the food product in an amount of from 0.01 to 1.5% by weight of the hydrated weight of the food product.

According to a preferred embodiment of the invention, the Biopolymer PS 87 is mixed in the form of an aqueous solution with food ingredients prior to dehydration thereof, the mixture subsequently being dried by a convenient means.

The following example illustrates this aspect of the invention:

EXAMPLE 9

A dehydrated vegetable soup mix.

Selected vegetables can be chopped and then dehydrated with the least heat necessary to drive off most of their natural moisture. This keeps them uncooked and retains their raw flavours, colours and vitamin content. These can then be mixed with the following ingredients:

|  | Parts by weight |
| --- | --- |
| Dehydrated chopped vegetables | 10 |
| Vegetable proteins | 25 |
| Monosodium glutamate | 8 |
| NaCl | 15 |
| Sodium nitrate | 0.05 |
| Milk powder | 30 |
| Sucrose | 7 |
| Wheat flour | 25 |
| Condiments | q.s. |
| Biopolymer PS 87 | 0.06 |

The resulting product will be observed to have excellent consistency and mouth-feel and viscosity when reconstituted with the conventional amounts of water. It will also exhibit a flavour and colour, when dehydrated, that is quite close to the undehydrated soup. The Biopolymer PS 87 can be added either prior to dehydration or thereafter, for instance, upon reconstitution. However, adding it prior to dehydration will be especially advantageous since it will require no extra processing steps and will result in a superior product, having all of the necessary ingredients except the water added upon reconstitution.

Similar improvements may be effective with other varieties of dehydrated soup products such as in the following:

EXAMPLE 10

Dehydrated per soup

A mixture of the following ingredients should first be prepared.

|  | Parts by weight |
| --- | --- |
| Pea flour | 8 |
| Onion powder | 0.5 |
| Salt | 1.5 |
| Biopolymer PS 87 | 0.10 |
| White pepper | 0.5 |
| Spices | 0.5 |
| Water | 89 |

The aqueous product can then be drum dried to obtain the desired dehydrated form.

The ingredients and proportions of a dehydrated soup mix or similar food product will of necessity vary, depending upon the type of soup being produced. The optimum level of Biopolymer PS 87 to use will also vary, depending upon the characteristics desired in the finished product.

EXAMPLE 11

| Celery soup | Parts by weight |
| --- | --- |
| Celery salt | 7 |
| Salt | 1 |
| Edible tallow | 7 |
| Biopolymer PS 87 | 0.02 |
| Soup flavouring or extracts of yeast or wheat | 25 |

EXAMPLE 12

| Cream of mushroom soup mix | Parts by weight |
| --- | --- |
| Whole milk powder | 27 |
| Wheat starch | 20 |
| Wheat flour | 15 |
| Dried mushrooms | 10 |
| Salt | 12 |
| Vegetable fat | 9 |
| Protex | 3 |
| Biopolymer PS 87 | 0.05 |
| Monosodium glutamate | 1.5 |
| Onion powder | 1.5 |

EXAMPLE 13

| Dehydrated tomato soup | Parts by weight |
| --- | --- |
| Potato flour | 64 |
| Onion powder | 5 |
| Tomato puree (25% solids) | 60 |
| Salt | 16 |
| Sugar | 12 |
| Biopolymer PS 87 | 0.15 |

-continued

| Dehydrated tomato soup | Parts by weight |
|---|---|
| Black pepper | q.s. |

In each case, the mixture should be dehydrated and then packaged in moisture-proof container.

Further information concerning dehydrated food products and their preparation is described in U.S. Pat. No. 3,694,236, the disclosure of which is incorporated herein by reference.

Dentifrice

The invention also relates to a liquid or pasty dentifrice and to a process for preparing such a liquid or pasty dentifrice. More specifically, the invention provides a liquid or pasty dentifrice comprising, uniformly incorporated therein, preferably in a proportion of 0.3 to 2 parts by weight per 100 parts by weight of the dentifrice, a thickening and suspending agent consisting of Biopolymer PS 87.

We have now found that a liquid or pasty dentrifice comprising Biopolymer PS 87 has improved properties compared with the conventional liquid or pasty dentifrice containing a xanthan gum, in that it exhibits unique pseudoplasticity whereby the dentifrice easily flows under a low pressure, and loses its flowability upon removal of the pressure. More particularly when the dentifrice in a container is to be extruded onto a toothbrush ready for use, it can be extruded with good flowability by a light extruding pressure, and as soon as it leaves the extrusion orifice, it loses its flowability but retains the shape as extruded.

The invention accordingly provides a liquid thixotropic gel dentifrice that is stable against phase separation of solid abrasive dentifrice particle ingredients which assentially consists of:

(i) 25 to 35% by weight of water;
(ii) 20 to 35% by weight of a humectant;
(iii) 0.5 to 2% by weight of a surfactant;
(iv) 0.3 to 2% by weight of Biopolymer PS 87; and
(v) 20 to 35% by weight of a solid particulate abrasive;

whereby the thixotropic gel dentifrice flows easily under low pressure and then extruded loses its flowability upon removal of extrusion pressure while retaining the shape as extruded.

The amount of Biopolymer PS 87 employed in the dentifrice is preferably from 0.5 to 1% by weight.

The dentifrice of this invention contains conventional well-known dentifrice ingredients such as humectants, detergents or surface active agents, flavouring materials, sweetening agents, abrasives, colouring materials, anti-caries agents, fungicidal or bacteriocidal agents, or water. The amount of these conventional dentifrice ingredients may be adjusted to within the conventional ranges. Most commonly, in the case of a liquid dentifrice, such a formulation consists of from 25 to 45% by weight of water, from 20 to 35% by weight of abrasives, from 20 to 35% by weight of humectants, from 0.5 to 2% by weight of detergents or surface active agents, from 0.3 to 2% by weight of Biopolymer PS 87, the remainder being other conventional dentifrice ingredients. In the case of a pasty dentifrice, the utilisable formulation consists of from 25 to 35% by weight of water, from 35 to 50% by weight of abrasives, from 15 to 30% by weight of humectants, from 0.5 to 2% by weight of detergents or surface active agents, from 0.3 to 2% by weight of Biopolymer PS 87, the remainder being other conventional dentifrice ingredients.

A part of Biopolymer PS 87 used as a thickening and suspending agent can be replaced by a known thickening and suspending agent for dentifrice. The suitable amount of such a known thickening and suspending agent is not more than about 1.4 times the weight of Biopolymer PS 87, preferably equal to the weight of Biopolymers PS 87 or less.

Examples of the conventional known thickening and suspending agents are carboxymethyl cellulose, its alkali metal salts, carrageenan, sodium alginate, hydroxyethyl cellulose, methyl cellulose tragacanth gum, locust bean gum, and tamarind seed-polysaccharide.

Examples of humectants include glycerol, sorbitol, maltitol, glucose, propylene glycol, polyethylene glycol and sodium pyrrolidone carboxylate.

Examples of the abrasives are dicalcium phosphate dihydrate, calcium pyrophosphate, anhydrous dicalcium phosphate, insoluble sodium metaphosphate, hydrated alumina, calcium carbonate, magnesium carbonate, magnesium oxide, and finely powdered silica.

Examples of the detergents or surface active agents are sodium lauryl sulphate, sodium N-lauroyl sarcosinate, α-olefin sulphonate, sodium 2-hydroxyalkyl sulphate, sodium laurylether sulphate, sodium coconut monoglyceride sulphate, sodium coconut monoglyceride sulphonate, a sodium salt of a monoester of lauroylethanolamide sulphosuccinic acid, polyoxyethylene fatty acid esters such as polyoxyethylene sorbitan monolaurate, polyoxyethylene sorbitan monopalmitate, polyoxyethylene sorbitan monostearate, or polyoxyethylene stearate having a degree of polymerisation of at least 25, and a polyoxyethylene polyoxypropylene block copolymer.

Examples of the flavour materials are peppermint oil, spearmint oil, sassafras oil, clove oil, sage oil, Eucalyptus oil, marjoram oil, lemon oil, cinnamon oil, orange oil, and sodium methyl salicylate.

The sweetening agents may, for example, be sodium saccharate.

Examples of the colouring materials, anti-caries agents, and fungicidal or bacteriocidal agents are sodium fluoride, tin fluoride, hexachlorophene, and sodium monofluorophosphate.

This aspect of the invention is further illustrated by the following Examples.

EXAMPLE 14

Liquid dentifrice

|  | Parts by weight |
|---|---|
| Calcium carbonate | 30.0 |
| Biopolymer PS 87 | 1.0 |
| Glycerol | 30.0 |
| Water | 36.36 |
| Sodium laurylsulphate | 1.5 |
| Sodium saccharate | 0.1 |
| Flavour | 1.0 |
| Fungicide | 0.04 |

The Biopolymer PS 87, fungicide and sodium saccharate should be pre-mixed, and with stirring, glycerol gradually added, followed by addition of water. By thorough mixing, the mixture will become viscous. Calcium carbonate should then be added to this mixture with stirring, and thoroughly dispersed. The flavour and sodium laurylsulphate can then be added, and the mixture stirred in vacuo to form a uniform composition as a liquid dentifrice.

EXAMPLE 15

Liquid dentifrice

|  | Parts by weight |
| --- | --- |
| Dicalcium phosphate dihydrate | 30 |
| Biopolymer PS 87 | 1.0 |
| Glycerol | 30.0 |
| Water | 36.36 |
| Sodium laurylsulphate | 1.5 |
| Sodium saccharate | 0.1 |
| Flavour | 1.0 |
| Fungicide | 0.04 |

In accordance with the above formulation, a liquid dentifrice can be prepared in the same way as in Example 14.

EXAMPLE 16

Pasty dentifrice

|  | Parts by weight |
| --- | --- |
| Dicalcium phosphate dihydrate | 45.0 |
| Biopolymer PS 87 | 0.5 |
| Carboxymethyl cellulose | 0.5 |
| Glycerol | 10.0 |
| Sorbitol | 10.0 |
| Water | 30.86 |
| Sodium laurylsulphate | 1.5 |
| Polyoxyethylene polyoxypropylene block copolymer | 0.5 |
| Sodium saccharate | 0.5 |
| Flavour | 1.0 |
| Fungicide | 0.04 |

In accordance with the above formulation, a pasty dentifrice can be prepared in the same way as Example 14.

Further data concerning this aspect of the invention is described in U.S. Pat. No. 3,963,832, the disclosure of which is incorporated herein by reference.

WATER BASE PAINT CONTAINING BIOPOLYMER PS 87

The invention also relates to water base paints and more particularly to dripless water base paints having an advantageous pseudoplastic or thixotropic body.

In general, water base paints are polymeric resin emulsions resulting from the polymerisation of monomers. Such paints contain a pigment and may also contain other ingredients such as extenders; anti-foaming agents; dispersion agents; freeze-thaw stabilisers; thickeners; and preservatives.

In a water base paint, water takes the place of the thinner in the conventional oil base paint, when the paint is applied upon a surface in a thin film, the water evaporates, and the resinous or rubber-like materials form a continuous film, where, by oxidation, polymerisation, or by coalescence of the resin particles, the film becomes water resistant.

The formulation of a water base paint is varied to suit its conditions of use. The binder or film forming agents are rubber-like materials and, as disclosed in the paint technology literature, may vary in composition. The following synthetic plastic semi-solids are particularly well known and are used as binders or film-forming agents in commercial water base paint formulations: styrene-butadiene copolymers or polystyrene in both post and preplasticised systems, polyacrylate emulsions; polyvinyl chloride emulsions; polyvinyl acetate emulsions; and vinyl acetate copolymer emulsions such as vinyl acetate-ethylene copolymer, polyvinyl chloride-vinyl acetate copolymer and polyvinyl acetate-butadiene copolymer emulsions. These synthetic water base paint binders are described as both emulsions and as synthetic latexes, the latex being preferred terminology. Natural latex, although disclosed in the literature as a binder or film-forming agent in water base paints is not generally used.

Those skilled in the art of formulating water base paints appreciate the need for the improvement of their properties in such important characteristics or properties as rollability or brushability while maintaining good antidrip characteristics; good flow and leveling to give a smooth glass-like finish; relatively uniform viscosity under changing conditions of temperature and pH; good hiding power with non-sag characteristics; good gel structure and strength; ease of manufacture; and particularly the need to improve water base paint composition having all or most of the aforementioned desirable properties.

The invention accordingly also provides a water base paint comprising a latex rubber-like water base paint binder, a pigment, an aqueous vehicle for said binder and pigment and an amount of Biopolymer PS 87 sufficient to give the paint pseudoplastic properties.

Suitable quantities of Biopolymer PS 87 for incorporating into the paint are from 0.01 to 4% preferably from 0.2 to 2% by weight of the paint.

In forming water base paints which contain an effective quantity of Biopolymer PS 87 to thicken said paint, the paint contains an aqueous emulsion latex composition containing a resinous film forming agent and a pigment. The paint may also contain other ingredients such as extenders, antifoaming agents, dispersion agents, freeze-thaw stabilisers and preservatives.

The invention also provides a process for forming a water base paint comprising latex rubber-like water base paint binder, a pigment which process comprises forming a pigment grind of the pigment and water together with Biopolymer PS 87, grinding the pigment and subsequently incorporating the pigment so treated into the paint binder together with other ingredients as desired.

The formulation of water base paints of the type comprising Biopolymer PS 87 and their preparation are described generally in U.S. Pat. No. 3,894,976, the disclosure of which is incorporated by reference.

This aspect of the invention is further illustrated by the following example, which describes the preparation of a water based emulsion paint.

EXAMPLE 17

A flat wall paint can be prepared by mixing together the following ingredients:

|  | Parts by weight |
| --- | --- |
| Water | 160 |
| Sodium salt of polymeric carboxylic acid | 14 |
| Benzyl ether of octyl phenol ethylene oxide: 100% active | 2 |
| Anti-foam | 4 |
| Ethylene glycol | 10 |
| Hexylene glycol | 30 |
| Microbiocide | 1 |
| Titanium dioxide | 300 |
| Aluminium silicate clay | 86 |

-continued

| | Parts by weight |
|---|---|
| Silica | 57 |
| 45% by weight aqueous acrylic emulsion | 397 |
| 2% solution of Biopolymer PS 87 | 100 |

The paint so obtained will be stable on storage at room temperature in that it will exhibit no gellation, no separation, smooth flow and no pigment flocculation.

Oil Well Drilling Fluid

The invention also relates to a novel drilling fluid and to its use in the drilling of oil wells, gas wells and the like in which viscous fluids are circulated within the well bore.

Drilling muds which are used in the drilling of oil wells, gas wells and the like are generally aqueous fluids which contain substantial quantities of clays and other colloidal materials. These colloidal materials assist in imparting the desired viscosity and gel strength to the fluid as required for the entrainment and suspension of drill clays and weighting agents and in the formulation of filter cake as needed for the reduction of fluid losses to the surrounding strata. The viscosity provided in drilling fluids by the use of colloidal clays and the like frequently can have an adverse effect in that the resulting fluids are difficult to pump and do not provide adequate lubrication of the drill bit. Thus, it would be desirable to provide drilling fluids which are more flexible in their viscosity characteristics so as to provide suspension of solids within the fluid as required for the filter cake without having an adverse effect upon the pumpability of the fluid and its ability to lubricate the drill bit.

Accordingly, the present invention also provides a drilling fluid which comprises Biopolymer PS 87. It has been found that drilling fluids which contain Biopolymer PS 87 are highly pseudoplastic such that they undergo a marked reduction in viscosity when subjected to shear force. This permits the fluids to have a very high viscosity when at rest or when subjected to slight shear so as to entrain and suspend the drill clays and weighting agents present in the fluid. At the same time, when drilling fluid is subjected to shear forces, as in pumping, the resulting viscosity is markedly decreased which provides for ease in pumping. Also, when the drilling fluid encounters the high shear forces generated by the drill bit, the fluid is greatly reduced in viscosity so as to provide improved lubrication of the drill bit.

The drilling muds of our invention can be prepared by the addition of Biopolymer PS 87 to an aqueous drilling fluid. Bipolymer PS 87 may be present at a concentration of about 0.05% to about 2.5% by weight or higher.

Solutions containing Biopolymer PS 87 may be employed as a drilling mud or fracturing fluid without the addition of other materials. Thus, for example, in drilling a formation which contains clay-type shales which would serve to increase the density of the drilling fluid, the drilling fluid may be a simple solution of the heteropolysaccharide in water. During drilling, the drill clays from the formation would then be picked up by the drilling fluid to increase its density.

In some cases, a weighting agent may be included in the drilling fluid. Typical of such weighting agents are barium sulphate, amorphous silica or calcium carbonate, lead sulphide, barium carbonate and the like. Also included in the drilling fluid is a preservative such as formaldehyde, paraformaldehyde, or sodium trichlorophenate, sodium pentachlorophenate and the like. The weighting agents are employed at a concentration which will provide the desired mud density and the preservatives are generally employed a concentration of about 0.001% to about 0.1% based on the weight of the fluids in the system.

Other additives, in addition to the weighting agents and preservatives, may also be present in the muds or similar fluids of the invention. As an example, the drilling fluid may also include gel forming materials such as bentonite and attapulgite clay and fluid loss control agents, such as starch and carboxymethyl cellulose. Still other types of additives which may be present are viscosity modifying agents such as ferro chrome lignosulphonate, sodium lignosulphonate, quebracho, and calcium lignosulphonate; calcium treating agents such as lime, calcium sulphate and calcium chloride; emulsifiers such as petroleum sulphonate, tall oil soap and sodium lignosulphonate and materials such as crude oil or diesel oil if an emulsion fluid is desired. The above listed additives will not normally all be present in a particular drilling mud or other fluid and the quantity of a particular additive will be determined to some extent by the other constituents of the fluid and the particular use intended for the fluid.

Biopolymer PS 87 may be also used in emulsion-type drilling and the base to water followed by intense mixing of the resultant solution with oil will result in a stable oil-in-water emulsion. Oil-in-water emulsions have low fluid loss properties and also have the desirable characteristics which are typical of emulsion-type drilling fluids.

The formulation of drilling fluids of the type comprising Biopolymer PS 87 and their preparation and use are described generally in U.S. Pat. No. 3,979,303, the disclosure of which is incorporated herein by reference.

This aspect of the invention is further illustrated by the following example which describes a typical drilling fluid.

EXAMPLE 18

A drilling fluid can be prepared by dissolving Biopolymer PS 87 in brine to provide a concentration of 0.3% by weight in terms of Biopolymer PS 87.

Tertiary Oil Recovery

Typically, oil is recovered from underground reservoirs via a series of sequential operations. A new well will generally produce a limited amount of oil as a result of release of internal pressure in the well. As this pressure becomes depleted, it is necessary to pump further quantities of oil by mechanical means. These measures recover only about 25% of the total oil stored in the reservoir. A great deal of oil is still trapped within the pores of the formation. Further enhancement of recovery can then be effected by secondary recovery. In one method of recovery a waterflood is carried out by pumping water into a well or series of wells, displacing part of the trapped oil from the porous rock and collecting the displaced oil from surrounding wells. However, waterflooding still leaves about 55–60% of the available oil trapped in the formation. The explanation for this phenomenon is that the water has a very low viscosity compared to the crude oil and tends to follow the path of least resistance, fingering through the oil and leaving large pockets untouched. In addition, surface forces in the formation tend to bind the oil and prevent its displacement.

A number of processes have been developed in recent years to recover further quantities of oil from these reservoirs by the use of mobility control solutions which enhance oil displacement by increasing the viscosity or permeability of the displacing fluid. Of interest are those enhanced recovery processes employing polymer flooding with a polysaccharide or polyacrylamide to increase the viscosity of the displacing fluid. Variations of this process include the use of surfactants and co-surfactants to release the oil from the rock formation. Certain polyacrylamides have been found to suffer such deficiencies as viscosity loss in brines and severe shear sensitivity.

We have now discovered that Biopolymer PS 87 is insensitive to salts in that it does not precipitate nor lose viscosity under normal conditions of use and is shear stable, thermostable and viscosity stable over a wide pH range. Biopolymer PS 87 is accordingly a good displacing agent for oil and is poorly absorbed on the elements of the porous rock formation and will develop viscosities appropriate to enhancing oil recovery (a viscosity of at least 150 poise at 20° C. for a 1% solution of Biopolymer PS 87).

The invention accordingly provides a mobility control solution for use in oil recovery comprising an aqueous solution of Biopolymer PS 87 in which the Biopolymer PS 87 forms from 0.005 to 0.5% by weight of the control solution. The aqueous solution can also comprise a salt such as sodium chloride.

The invention also provides a process for the recovery of crude oil from an oil-bearing subterranean formation which comprises injecting into the formation a mobility control aqueous solution comprising from 0.005 to 0.5% by weight of Biopolymer PS 87.

It is to be understood that there may be conditions and factors that make impracticable the transportation of large volumes of mobility control solution for injection into oil-containing reservoirs. For such purposes, it may be convenient to provide the Biopolymer PS 87 in a dried or desiccated form ready for reconstitution with water or brine on site as and when required. If it is necessary to store the Biopolymer PS 87 solution before use, the addition of formaldehyde at a concentration of from 0.02 to 1% by weight of the control solution will generally prevent deteriorative changes due to contaminant micro-organisms.

Further data concerning this aspect of the invention is described in British Pat. No. 1,531,970, the disclosure of which is incorporated by reference.

Suspension polymerisation

The invention also relates to suspension polymerisation in its broadest sense, such as the procedures relative to monomers and comonomers as set out in Encyclopedia of Polymer Science and Technology, Vol. 13.

Suspension polymerisation is developed from the old "Bead Process" originally introduced for polystyrene production; this is a type of mass polymerisation in that small droplets of liquid monomer are dispersed in water and caused to polymerise to solid spherical particles.

The chief problems in suspension polymerisation is in the formation and maintenance of a uniform suspension of the monomer droplets as they are slowly transformed from a sticky material to a rigid granular solid, without coalescence or aggregation of the particles into a conglomerate mass. The operation requires the use of proper agitation and stabilising agents for maintaining the suspension of the droplets, or particles, with a minimum of interaction.

The procedures used in suspension polymerisation are much the same regardless of the monomer charged, the dispersion of the monomer, as a liquid in small droplets, into an agitated stabilising medium consisting of water containing small amounts of suspension and dispersion agents. The catalyst (initiator) is added to the reaction mixture after the addition of the monomer.

The suspension material is conventionally a protective colloid agent (water soluble high polymers), such as the widely used protective colloids: carboxymethyl cellulose, a 1:1 mixture of carboxymethyl cellulose and starch, hydroxyethyl cellulose, methyl cellulose, polyacrylic acid, polyvinyl alcohol, gelatin, alginates, gum acacia, and gum tragacanth.

It has been discovered that benefits can be obtained in the production of solid, particulate polymer by the suspension polymerisation of liquid monomer by the use as suspension agent of Biopolymer PS 87. The amount of Biopolymer PS 87 present is from 0.1 to 5% by weight based on monomer charge to the process.

The invention accordingly provides a process for the aqueous suspension polymerisation of a liquid monomer to a particulate polymer in which the monomer is acrylic acid or its polymerisable derivatives, methacrylic acid or its polymerisable derivatives, esters or ethers of vinyl alcohol, vinylidene chloride, styrene or methylstyrene, the process comprising conducting the polymerisation in the presence of from 0.1 to 5% by weight of Biopolymer PS 87.

The improvement in suspension agent is applicable to all monomers which can be polymerised by the suspension agent combination improvement is applied to the monomers: (1) The polymerisable derivatives of acrylic acid and methacrylic acid, including methacrylic acid itself, methyl acrylate, ethyl acrylate, phenylethyl acrylate, methoxyethyl acrylate, methyl methacrylate, ethyl methacrylate, isopropyl methacrylate, phenyl methacrylate, phenylethyl methacrylate, methoxyethyl methacrylate, acylonitrile and methacrylonitrile; (2) esters and ethers of vinyl alcohol, such as vinyl chloride, vinyl acetate, vinyl propionate, vinyl butyrate vinyl methyl ether, vinyl ethyl ether and vinyl phenyl ether; (3) vinylidene chloride; and (4) styrene and its alpha lower alkyl derivatives, such as styrene, and alpha methylstyrene.

In one particular embodiment using methyl methacrylate as the monomer, the Biopolymer PS 87 is present in an amount on the order of 0.1 to 1% by weight, based on methyl methacrylate charged.

In another particular embodiment using styrene as the monomer, the Biopolymer PS 87 is present in an amount of the order of 0.1 to 0.5% by weight, based on styrene charged.

In still another particular embodiment using styrene as the monomer, the Biopolymer PS 87 is present in an amount on the order of 2.0 to 4.0% by weight, based on styrene charged.

Further details of the procedure that can be employed and worked examples of the process of suspension polymerisation in the presence of Biopolymer PS 87 are substantially similar to that described in U.S. Pat. No. 3,852,257, the disclosure of which is incorporated herein by reference.

The invention also relates to an aqueous, built liquid detergent composition with improved physical storage stability.

It is well-known that one of the major problems encountered with aqueous, built liquid detergent compositions is that of ensuring a sufficient physical storage stability of these compositions. If no special measures are taken, the builder salts and, as the case may be, other ingredients present in such compositions, tend to separate out, especially when higher levels of these salts are incorporated.

In the art, consequently, there have been various proposals to include particular stabilising agents in such compositions, in order to stably suspend these builder salts. Typical examples of such known stabilising agents are synthetic polymers such as maleic anhydride copolymers with ethylene, methyl vinylether, polyacrylates, etc. Normally, these polymers are used at a level of 0.5 to 2% by weight. Although a satisfactory storage stability can be obtained with such polymers, often the viscosity of the compositions thus stabilised is higher than desired, and the viscosity should be reduced by proper means. A careful balance between stability and viscosity is consequently required.

It has now been found that the inclusion of very low levels of Biopolymer PS 87 in an aqueous, built liquid detergent composition imparts excellent physical storage stability thereto, the compositions thus stabilised having an acceptable viscosity, often lower than that of compositions with other polymers of the prior art.

The invention accordingly also provides an aqueous, built liquid detergent composition comprising an active detergent material, a builder and, as a stabilising agent, Biopolymer PS 87 as herein defined.

The Biopolymer PS 87 is used in the aqueous, built liquid detergent composition of the invention in an amount of 0.05 to 1, preferably 0.1 to 0.5% by weight of the total composition. The liquid detergent compositions of the invention furthermore comprise as essential ingredient an active detergent material, which may be an alkali metal or alkanol amine soap of a $C_{10}$–$C_{24}$ fatty acid, including polymerised fatty acids or an anionic, nonionic, zwitterionic or amphoteric synthetic detergent material, or mixtures of any of these.

Examples of anionic synthetic detergents are salts (including sodium, potassium, ammonium, and substituted ammonium salts such as mono-, di- and triethanolamine salts) of $C_9$–$C_{20}$ alkylbenzenesulphonates, $C_8$–$C_{22}$ primary or secondary alkanesulphonates, $C_8$–$C_{24}$ olefinsulphonates, sulphonated polycarboxylic acids, prepared by sulphonation of the pyrolysed product of alkaline earth metal citrates, e.g. as described in British Patent Specification No. 1,082,179, $C_8$–$C_{22}$ alkylsulphates, $C_8$–$C_{24}$ alkylpolyglycolethersulphates (containing up to 10 moles of ethylene oxide); further examples are described in "Surface Active Agents and Detergents" (Vol. I and II) by Schwartz, Perry and Berch.

Examples of nonionic synthetic detergents are the condensation products of ethylene oxide, propylene oxide and/or butyleneoxide with $C_8$–$C_{18}$ alkylphenols, $C_8$–$C_{18}$ primary or secondary aliphatic alcohols, $C_8$–$C_{18}$ fatty acid amides; further examples of nonionics include tertiary amine oxides with one $C_8$–$C_{18}$ alkyl chain and two $C_{1-3}$ alkyl chains. The above reference also describes further examples of nonionics.

The average number of moles of ethylene oxide and/or propylene oxide present in the above nonionics varies from 1–30; mixtures of various nonionics, including mixtures of nonionics with a lower and a higher degree of alkoxylation, may also be used.

Examples of amphoteric or zwitterionic detergents are N-alkylamino acids, sulphobetaines, condensation products of fatty acids with protein hydrolysates, but owing to their relatively high costs they are usually used in combination with an anionic or a nonionic detergent. Mixtures of the various types of active detergents may also be used. Soaps (in the form of their sodium, potassium and substituted ammonium salts such as triethanolamine salts) of $C_{10}$–$C_{24}$ fatty acids, as well as of polymerised fatty acids, may also be used, preferably in conjunction with an anionic and/or nonionic synthetic detergent, and may exert a beneficial influence on the foaming behaviour of the final composition.

The amount of the active detergent material varies from 1 to 60%, preferably from 2 to 40 and especially preferably from 5 to 25%; when mixtures of, e.g. anionics and nonionics are used, the relative weight ratio varies from 10:1 to 1:10, preferably from 6:1 to 1:6. When a soap is also incorporated, the amount thereof is from 1 to 40% by weight.

The liquid compositions of the invention further contain up to 60% of a suitable builder, such as sodium, potassium and ammonium or substituted ammonium pyro- and tripolyphosphates, -nitrilotriacetates, -etherpolycarboxylates, -citrates, -carbonates, -orthophosphates, zeolites, carboxymethyloxysuccinate, etc. Particularly preferred are the polyphosphate builder salts, nitrilotriacetates, zeolites, and mixtures thereof. In general, the builders are present in an amount of 1 to 60, preferably 5 to 50% by weight of the final composition.

The amount of water present in the detergent compositions of the invention varies from 5 to 70% by weight.

Other conventional materials may also be present in the liquid detergent compositions of the invention, for example soil-suspending agents, hydrotropes, corrosion inhibitors, dyes, perfumes, silicates, optical brighteners, suds boosters, suds depressants, germicides, anti-tarnishing agents, opacifiers, enzymes such as proteases, amylases and cellulases, fabric-softening agents, oxygen-libterating bleaches such as hydrogen peroxide, sodium perborate or percarbonate, diperisophthalic anhydride, with or without bleach precursors, buffers and the like. In this respect it is often advantageous to include a small amount of a salt, such as NaCl, since this may improve the efficacy of Biopolymer PS 87.

The invention will be further illustrated by way of the following Example.

EXAMPLE 19

The following liquid compositions were prepared:

| Composition | % by weight | | | | | | |
|---|---|---|---|---|---|---|---|
|  | A | B | C | D | E | F | G |
| $C_{13}$–$C_{15}$ primary alcohol, condensed with 7 moles of ethylene oxide plus propylene oxide (weight ratio of 92:8 (EO:PO) | 8 | 8 | 10 | — | 5 | — | 8 |
| Sodium dodecyl benzene sulphonate | — | — | — | 10 | 5 | 10 | — |
| Anhydrous sodium tripolyphosphate | 20 | 20 | 20 | 20 | 20 | 20 | 20 |
| Anhydrous potassium tripolyphosphate | — | 4 | — | — | — | — | 4 |

-continued

| Composition | % by weight | | | | | | |
|---|---|---|---|---|---|---|---|
| | A | B | C | D | E | F | G |
| Alkaline water glass (33% aqueous solution) | — | — | 10 | — | 10 | 10 | — |
| Sodium carboxymethylcellulose | — | — | 0.5 | 0.5 | 0.5 | 0.5 | — |
| Glycerol | 10 | 10 | — | 10 | — | — | 10 |
| Borax | 8 | 8 | — | 8 | — | — | 8 |
| Fluorescer | — | — | 0.1 | 0.1 | 0.1 | 0.1 | — |
| Biopolymer PS 87 (as herein defined) | 0.25 | 0.1 | 0.15 | 0.15 | 0.15 | 0.15 | 0.25 |
| Water | bal. | bal. | bal. | bal. | bal. | bal. | bal. |

The products had the following physical properties:
A: viscosity about 10 poise; still stable after more than 3 months' storage at 23° C.
B: viscosity 2.8 poise at 100 sec$^{-1}$; still stable after 1 month's storage at 23° C.
C: minute exudation (<1%) after storage for 1 week at 23° C.
D: thin and pourable; no signs of instability after storage for 1 week at 23° C.
E: idem.
F: idem.
G: viscosity about 10 poise; still stable after 3 months' storage at 23° C.

More specific uses of Biopolymer PS 87 are given below with an indication of the benefits to be expected.

FOOD APPLICATIONS OF BIOPOLYMER PS 87

Bakery Fillings
Biopolymer PS 87 in bakery fillings will allow cold makeup. Texture, mouthfeel, and flavour release are excellent and filling is not absorbed by pastry.

Bakery Flavour Emulsions
Excellent stability and a smooth-textured, pourable body can be obtained. Compared to conventionally stabilised bakery flavour emulsions, those stabilised with Biopolymer PS 87 offer savings in preparation time.

Canned Foods
Biopolymer PS 87 can provide excellent viscosity control under processing conditions, including improved ease of pumping and filling operation due to shear-thinning properties. Partial starch replacement permits faster heat penetration, while maintaining nutritional quality and appearance of the food.

Dry Mixes
Biopolymer PS 87 can provide rapid, high viscosity build-up in cold or hot systems and can permit easy preparation of mayonnaise, milk shakes, sauces, gravies, and beverages having excellent texture, mouthfeel and flavour release.

Frozen Foods
Excellent emulsion and suspension stability and maintenance and control of syneresis of dressings, sauces, and gravies during freeze-thaw and heating cycles can be provided with Biopolymer PS 87. The freezethaw stability of starch-thickened products can be significantly improved by the incorporation of small amounts of Biopolymer PS 87.

Juice Drinks
Used at low concentrations, Biopolymer PS 87 can be effective in suspending fruit pulp for long periods of time, thus imparting uniformity of flavour, body consistency, and mouth-feel.

Pourable Dressings
Biopolymer PS 87, at concentrations considerably lower than other competitive gums, can impart superior emulsion stability, easier pumpability, less-gummy mouthfeel, more cling, excellent pourability at refrigerated temperature, and better flavour release due to its pseudoplastic nature.

Relish
The use of Biopolymer PS 87 in relishes can require no cooking in preparation, and loss of liquor during filling operation can be eliminated. Cling of relish and liquor to hot dogs and hamburgers can be improved, preventing soggy rolls and buns.

Syrups
The rheological properties of Biopolymer PS 87 can promote excellent pourability and cling to ice cream, fruits, pancakes, etc., as well as controlled penetration and run-off.

Slimming Foods
Biopolymer PS 87 can be employed as a bulking agent in slimming foods and in special medical diets.

Beer
Biopolymer PS 87 can be employed as a bodying agent in beer.

INDUSTRIAL APPLICATIONS OF BIOPOLYMER PS 87

Abrasives
Due to Biopolymer PS 87's low viscosity under high shear, rapid grinding action and fast removal of cuttings can be provided, along with excellent suspension of abrasives.

Adhesives
The rheological properties of Biopolymer PS 87 can permit controlled adhesive penetration. Adhesives will pump readily and have low viscosity on application, yet have high viscosity under low-shear conditions. Water release during drying can be fast.

Agricultural
Biopolymer PS 87 can be used as a suspending agent for herbicides, pesticides, fertilisers, and fungicides. Due to its excellent control of drift and cling during spraying, longer contact time can be possible. It can behave as an excellent stabiliser for flowable agrochemicals.

Ceramics
Biopolymer PS 87 can suspend ingredients in glaze and maintain viscosity. Extrusions can be lubricated and green strength can be improved.

Cleaners
The rheological properties of Biopolymer PS 87 can promote cling to vertical surfaces for longer contact time and can make possible formulation of gel-type acid and alkali cleaners for industrial applications.

Gels
Biopolymer PS 87 borax can act as a gelling agent in explosives. Biopolymer PS 87-iron gels can be functional in reducing usage of urea-formaldehyde adhesives in particle board.

Mining

Biopolymer PS 87 can control settling rate of ores during sedimentation, can act as a flocculant in separation processes, and can provide foam stabilisation. In slurry pumping, it can give up to 65% drag reduction and can also suspend—especially under low-shear conditions.

Paper

Biopolymer PS 87 can be used as an antimigrant in the paper industry as a rheology modifier for high-solids size press and roll coatings, wet-end formation aid, suspension of raw starch for jet cookers, and dewatering control of air knife coatings.

Pigments

Biopolymer PS 87 can provide suspension of slurried pigments during shipment and storage and can help control reagglomeration.

Polish

Biopolymer PS 87 can provide solids suspension in shoe polish, abrasive suspension in silver and brass polish, and emulsion stabilisation in wax polish.

Textile

As a suspending agent for dye pigments, Biopolymer PS 87 can control application in space printing and Kuester dyeing and acts as flow modifer during printing application.

Wallpaper

Biopolymer PS 87 can be used as a flow modifier and suspending agent during printing.

Welding Ends

Biopolymer PS 87 can lubricate during extrusion and can provide green strength.

Deodorant Gels

Deodorant gels made with Biopolymer PS 87 can be thermally reversible (when filled hot, they gel upon cooling). Firm, rubbery gels can be produced which slowly release deodorants.

Fire fighting

Due to its high viscosity at low concentrations, Biopolymer PS 87 can improve the drop pattern and the cling of the fire-fighting fluid to trees and shrubs.

Paper sizing

Use of Biopolymer PS 87 by the paper industry can enhance the efficiency of rosin-alum sizes, increases Mullen reading, and can improve internal water resistance.

Suspensions

The high yield stress value of Biopolymer PS 87 solutions can produces stable suspensions of a variety of materials.

Blasting explosives

Besides being compatible with high concentrations of inorganic nitrates, the Biopolymer PS 87 can easily be gelled to produce water-resistant slurries.

Various photographic processing

Biopolymer PS 87 can be highly compatible with photoprocessing solutions and can be thermally reversible within the temperature range of photo-processing. Smooth surfaces with low syneresis will result.

Soil erosion

Biopolymer PS 87 can be employed successfully in preventing soil erosion.

Biopolymer PS 87 can also be used in other food or industrial applications such as:

Ink

Biopolymer PS 87 can be used as a suspending agent and stabiliser for water-based and emulsion inks and can provide controlled penetration and water release under uniform gloss.

In Suspending Applications

For example, suspension of protein solids in calf milk replacers; shampoos for suspension of anti-dandruff agents.

Freezing compositions

Solutions of Biopolymer PS 87 at concentrations in the range of from 1 to 6% w/v provide gels which do not flow at ambient temperatures. Such gels can be made in the presence of high electrolyte concentrations and are suitable as freezing compositions for cooling duties. For example, a gel containing 3% w/v Biopolymer PS 87 and 22% w/v NaCl withstands repeated freezing and thawing without loss of the non-flow property indicating that there is no release of free electrolyte solution.

In Stabilisation of emulsions, for example, Hand creams; Foams; Wax polishes; Ice Cream; Margarine and other non-dairy spreads; Chocolate; Cosmetics, such as lipstick.

In Stabilisation of foams, for example, Milk Shakes; Beers.

In Gel type "cling" applications, for example, Acid/neutral cleaners; Derusting and iron-stain removal in baths; Denture fixatives.

In Other gel applications, for example, Reconstituted fruit; Shower wash/shampoos In Thickening applications, for example, Yoghurt, improved mouth feel and texture; Ice cream; Pie fillings; Jams and preserves.

In Other applications, for example, Reconstitution of tobacco leaves; Bakery with low gluten flour; Antiredeposition.

The above mentioned uses of Biopolymer PS 87 are to be understood as non-limiting and merely as exemplary of the many uses to which the heteropolysaccharide can be put.

What is claimed is:

1. An edible composition comprising a thickening or suspending amount of Biopolymer PS 87 wherein said Biopolymer PS 87 is a heteropolysaccharide which comprises from 40 to 45% by weight of glucose, from 10 to 20% by weight galactose, from 25 to 30% by weight mannose, from 16 to 13% by weight glucuronic acid and from 0 to 1.5% by weight fucose, a 1% by weight solution of said Biopolymer PS 87 having pseudoplastic properties, a consistency at 20° C. of at least 150 poise and a yield stress value at 20° C. of at least 30 dynes/cm$^2$.

2. A composition according to claim 1 additionally comprising a tetra-alkali metal phosphate, an edible calcium salt and a gum.

3. A process for forming a cold milk gel comprising the steps of adding to cold milk a composition according to claim 2 and agitating the milk composition to form a gel.

4. A salad dressing comprising a thickening or suspending amount of Biopolymer PS 87 wherein said Biopolymer PS 87 is a heteropolysaccharide which comprises from 40 to 45% by weight of glucose, from 10 to 20% by weight galactose, from 25 to 30% by weight mannose, from 16 to 13% by weight glucuronic acid and from 0 to 1.5% by weight fucose, a 1% by weight solution of said Biopolymer PS 87 having pseudoplastic properties, a consistency at 20° C. of at least 150 poise and a yield stress value at 20° C. of at least 30 dynes/cm$^2$.

5. A salad dressing according to claim 4, further comprising an edible oil, water, an emulsifier, cooked starch, an acidifying ingredient, and salt.

6. A method of making a spoonable salad dressing according to claim 4, which comprises the steps of forming a first mixture containing said Biopolymer PS 87 and water; forming a second mixture comprising water together with cooked starch, emulsifier and salt; blending the first mixture and the second mixture to form a combined first-second mixture with edible oil and with acidifying ingredient until a substantially uniform mixture is obtained; and emulsifying the uniform mixture to obtain a spoonable salad dressing.

* * * * *